(12) United States Patent
Sampson et al.

(10) Patent No.: US 6,869,767 B1
(45) Date of Patent: Mar. 22, 2005

(54) **DETECTION OF *STREPTOCOCCUS PNEUMONIAE* AND IMMUNIZATION AGAINST *STREPTOCOCCUS PNEUMONIAE* INFECTION**

(75) Inventors: Jacqueline S. Sampson, College Park, GA (US); Katherine E. Morrison, Columbia, SC (US); Jennifer Crook Whitmon, Stockbridge, GA (US); Edwin Ades, Atlanta, GA (US); George M. Carlone, Stone Mountain, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/168,602

(22) PCT Filed: Jun. 14, 1999

(86) PCT No.: PCT/US99/13421

§ 371 (c)(1),
(2), (4) Date: Jun. 21, 2002

(87) PCT Pub. No.: WO00/77254

PCT Pub. Date: Dec. 21, 2000

Related U.S. Application Data
(60) Provisional application No. 60/138,894, filed on Jun. 11, 1999.

(51) Int. Cl.[7] .................................................. C12Q 1/68
(52) U.S. Cl. ..................... 435/6; 435/91.1; 435/91.2; 435/975; 536/23.7; 536/24.32; 536/24.33
(58) Field of Search .............................. 536/23.7, 24.32, 536/24.33; 435/6, 975, 91.1, 91.2

(56) References Cited

U.S. PATENT DOCUMENTS

| | | | |
|---|---|---|---|
| 4,683,202 A | 7/1987 | Mullis | 435/91 |
| 4,965,188 A | 10/1990 | Mullis et al. | 435/6 |
| 5,422,427 A | 6/1995 | Russell et al. | 530/350 |
| 5,545,522 A | 8/1996 | Van Gelder et al. | 435/6 |
| 5,578,467 A | 11/1996 | Schuster et al. | 535/91.2 |
| 5,624,833 A | 4/1997 | Gelfand et al. | 435/194 |
| 5,854,416 A | 12/1998 | Sampson et al. | 536/23.7 |

FOREIGN PATENT DOCUMENTS

| | | | |
|---|---|---|---|
| EP | 0 622 081 A | | 11/1994 |
| WO | 98/18930 | * | 5/1998 |

OTHER PUBLICATIONS

Sampson. Submitted (Apr. 1996). Gencore Accession No. U3509.*

Centers for Disease Control and Prevention, "Prevention of pneumococcal disease: Recommendation of the Advisory Committee on Immunization Practices," (ACIP), 1997 Morbid. Mortal. Weekly Rep. (RR–8) 46:1–24 (Abstract).

Crook et al., "Immunoreactivity of five monoclonal antibodies against the 37–kilodalton common cell wall protein (PsaA) of *Streptococcus pneumoniae*," Clin. Diagn. Lab. Immunol. 5:205–210 (1998).

Henrichsen, "Six newly recognized types of *Streptococcus pneumoniae*," J. Clin. Microbiol. 33:2759–2762 (1995).

Kalin et al., "Diagnosis of pneumococcal pneumonia: a comparison between microscopic examination of expectorate, antigen detection, and cultural procedures," Scand. J. Infect. Dis. 15:247–255 (1983).

Novak, R. et al., "Penicillin tolerance genes of *Streptococcus pneumoniae*: the ABC type maganese permease complex Psa," Mol. Microbiology 29(5):1285–1296 (Sep. 1998).

Obaro et al., "Carriage of pneumococci after pneumococcal vaccination," Lancet 348:271–272 (1996).

Russell et al, "Monoclonal antibody recognizing a species–specific protein from *Streptococcus pneumoniae*," J. Clin. Microbiol. 28:2192–2195 (1990).

Sampson et al., "Limited diversity of *Streptococcus pneumoniae* psaA among pneumococcal vaccine serotypes," Infection and Immunity 65(5):1967–1971 (May 1997).

Sampson, J.S. et al., "Cloning and nucleotide sequence analysis of psaA, the *Streptococcus pneumoniae* gene encoding a 37–kilodalton protein homologous to previously reported *Streptococcus* sp. adhesins," Infection and Immunity 62(1): 319–324 (Jan. 1, 1994).

Talkington et al., "Protection to mice against fatal pneumococcal challenge by immunization with pneumococcal surface adhesin A (PsaA)," Microbial Pathogenesis 21(1):17–22 (Jul. 1996).

(List continued on next page.)

Primary Examiner—Jennifer E. Graser
(74) Attorney, Agent, or Firm—Needle & Rosenberg, PC.

(57) ABSTRACT

The present invention relates to oligonucleotide primers, and methods of diagnosis using the primers, wherein particular primer pairs prime the universal amplification of an amplicon for specific *Streptococcus pneumoniae* from all 90 known serotypes. The amplicon includes at least a portion of the psaA gene of *Steptococcus pneumoniae*. In the methods, amplification of a biological sample using the primer pairs of the invention provide an amplicon only if the sample contains a serotype of *Streptococcus pneumoniae*. The invention further relates to an isolated nucleic acid including a nucleic acid amplicon obtained using a pair of oligonucleotide primers of the invention. In still a further aspect, the invention discloses a polypeptide including an amino acid sequence encoded by a nucleic acid amplicon obtained using oligonucleotide primers. Additionally, methods of stimulating an immune response against a serotype of *Streptococcus pneumoniae* in a mammal include either administering a polypeptide encoded by a nucleic acid amplicon obtained using the pair of oligonucleotide primers of the invention, or administering a nucleic acid containing a nucleic acid amplicon obtained using the pair of oligonucleotide primers of the invention.

9 Claims, 2 Drawing Sheets

OTHER PUBLICATIONS

Tharpe et al., "Comparison of a pneumoccocal common protein (PsaA) antibody ELISA and a PsaA immune complex ELISA for detection of pneumococcal serum antibody," *Pathobiology* 66:77–83 (1998).

Tharpe et al., "Purification and seroreactivity of pneumococcal surface adhesin A (PsaA)," *Clin. Diagn. Lab. Immunol.* 3(2):227–229 (Mar. 1996).

Tharpe et al, "The utility of a recombinant protein in an enzyme immunoassay for antibodies against *Streptococcus pneumoniae*," Abstr. V–2, p. 617, American Society for Microbiology, Washington, D.C. (1994).

Toikka et al., "Pneumolysin PCR–based diagnosis of invasive pneumococcal infection in children," *J. Clin. Microbiol.* 37:633–637 (1998).

* cited by examiner

DETECTION OF *STREPTOCOCCUS PNEUMONIAE* AND IMMUNIZATION AGAINST *STREPTOCOCCUS PNEUMONIAE* INFECTION

The present application is 35 U.S.C. § 371 national phase application from, and claims priority to, revived international application PCT/US99/13421, filed Jun. 14, 1999 (published under PCT Article 21(2) in English), which claims priority to U.S. provisional patent application Ser. No. 60/138,894, filed Jun. 11, 1999, which applications are incorporated herein in their entirety by reference.

FIELD OF THE INVENTION

This invention relates to the detection and treatment of *Streptococcus pneumoniae* infection. Specifically, the present invention relates to diagnostic assays and kits for detecting the presence of *Streptococcus pneumoniae* in a sample and to vaccines for use against *Streptococcus pneumoniae*. More specifically, the present invention relates to PCR assays for the presence of *Streptococcus pneumoniae* surface adhesin A protein (PsaA) and to vaccines raised against a portion of PsaA encoded by a PCR product that is provided using specific primers.

BACKGROUND OF THE INVENTION

*Streptococcus pneumoniae* is frequently isolated from the young, the elderly, and the immunocompromised as the etiologic agent of a broad range of diseases (Centers for Disease Control and Prevention, "Prevention of pneumococcal disease: Recommendations of the Advisory Committee on Immunization Practices" (ACIP), 1997 Morbid. Mortal. Weekly Rep. (RR-8) 46:1–24). A number of diagnostic assays for the detection of *Streptococcus pneumoniae* have been developed and are described in the literature. Unfortunately they are not sufficiently definitive, reliable, or sensitive to be used on a routine basis (Sampson et al. 1994, "Cloning and nucleotide sequence analysis of psaA, the *Streptococcus pneumoniae* gene encoding a 37-kilodalton protein homologous to previously reported *Streptococcus* sp. adhesins", Infect. Immun. 62:319–324). The large number of pneumococci currently known (90 different serotypes) increases the challenge of diagnosis and further complicates assay development and vaccine development.

*Streptococcus pneumoniae* normally colonizes the nasopharynx and can be found in 5–10% of healthy adults and 20–40% of healthy children. *S. pneumoniae* is responsible for a variety of infections including common "strep throat," otitis media, sinusitis, meningitis, tracheitis, bronchitis, rheumatic fever, and community-acquired pneumonia. It can also spread from the nasopharyngeal cavity into the central nervous system, heart valves, bones, joints, and peritoneal cavity. The organism typically binds to the upper respiratory tract. It is transmitted person-to-person via droplets in the air; transmission through direct contact is also thought to occur.

Generally streptococcal infections affect the lungs in less than 5% of cases. Such lung infections, however, progress with great rapidity and severity, despite treatment with antibiotics. This form of pneumonia is difficult to control and may last for weeks. Although severe pneumonia can be caused by a wide variety of bacteria, as well as by viruses, streptococcal infection accounts for about 55% to 76% of cases. About 2 million Americans get pneumonia each year, with 40,000 to 70,000 deaths reported. Pneumonia ranks sixth among all categories of disease as a cause of death.

Despite the many testing technologies available to physicians, it is sometimes very difficult to determine which species of bacteria is responsible for the illness; in up to half the cases no etiological agent can be identified.

Considerable effort has been invested in developing a vaccine against *Streptococcus pneumoniae*. An immunogenic species-common protein has been identified (Russell et al. 1990, "Monoclonal antibody recognizing a species-specific protein from *Streptococcus pneumoniae*", J. Clin. Microbiol. 28:2192–2195; U.S. Pat. No. 5,422,427). In these references, the 37 kDa protein of the present invention is referred to pneumococcal fimbrial protein A. This 37 kDa *S. pneumoniae* protein has been the focus of several studies and is now designated pneumococcal surface adhesin protein A (PsaA). Immunoblot analysis studies using anti-PsaA monoclonal antibody showed that PsaA is common to all 23 pneumococcal vaccine serotypes known at that time (i.e., about 1990). Enzyme-linked-immunosorbent assay studies have indicated that patients with pneumococcal disease show an antibody increase in convalescent-phase serum to PsaA compared with acute-phase serum antibody levels (Tharpe et al. 1995, "Purification and seroreactivity of pneumococcal surface adhesin A (PsaA)". Clin. Diagn. Lab. Immunol. 3:227–229; Tharpe et al. 1994, "The utility of a recombinant protein in an enzyme immunoassay for antibodies against *Streptococcus pneumoniae*", Abstr. V-2, p. 617,1994. American Society for Microbiology, Washington, D.C.). Additionally a limited in vivo protection study showed that antibodies to the 37-kDa protein protect mice from lethal challenge (Talkington et al. 1996, "Protection of mice against fatal pneumococcal challenge by immunization with pneumococcal surface adhesin A (PsaA)", Microbial Pathogenesis 21:17–22).

The gene encoding PsaA from *S. pneumoniae* strain R36A (an unencapsulated strain) has been cloned in *E. coli* and sequenced. This serotype does not, however, contain a nucleic acid encoding a 37 kDa protein that is highly conserved among the various serotypes (Sampson et al. 1994). This particular nucleic acid and polypeptide, therefore, are of limited value for use as diagnostic reagents, in prevention or treatment of infection, or in vaccine development.

U.S. Pat. No. 5,854,416 provides a nucleic acid encoding the 37-kDa protein from serotype 6B of *Streptococcus pneumoniae*. Isolated nucleic acids comprising a unique fragment of at least 10 nucleotides of the 37-kDa protein are also provided. The patent further discloses purified polypeptides encoded by the nucleic acid encoding the 37-kDa protein, as well as nucleic acids comprising a unique fragment of at least 10 nucleotides coding for the 37-kDa protein. In addition, antibodies are provided which selectively bind the polypeptides encoded by the nucleic acid encoding the 37-kDa protein and the nucleic acids comprising a unique fragment of at least 10 nucleotides of the 37-kDa protein. The patent additionally provides vaccines comprising immunogenic polypeptides encoded by the nucleic acid encoding the 37-kDa protein and by the nucleic acids comprising a unique fragment of at least 10 nucleotides of the 37 kDa protein. Further provided is a method of detecting the presence of *Streptococcus pneumoniae* in a sample comprising the steps of contacting a sample suspected of containing *Streptococcus pneumoniae* with nucleic acid primers capable of hybridizing to a nucleic acid comprising a portion of the nucleic acid encoding the 37-kDa protein, amplifying the nucleic acid and detecting the presence of an amplification product, the presence of the amplification product indicating the presence of *Streptococcus* pneumoniae in the sample. Further provided are and methods of detecting the presence of Streptococcus pneumoniae in a sample using antibodies or antigens, methods of preventing and treating Streptococcus pneumoniae infection in a subject.

Sampson et al. (1997, "Limited diversity of Streptococcus pneumoniae psaA among pneumoccocal vaccine serotypes". Infection and Immunity, 65(5):1967–1971) show that the pneumococcal surface adhesin A (PsaA) protein belongs to a group of proteins designated the lipoprotein receptor 1 antigen family. The gene encoding PsaA from an encapsulated strain of pneumococcal serotype 6B was cloned and sequenced. The peptide sequence was compared to that of homologs found in S. pneumoniae serotype 2, viridans streptococci, and Enterococcus faecalis. Identity values among the deduced peptides ranged from 57 to 98%. The polymorphism of psaA was examined among the 23 encapsulated vaccine serotypes by using PCR-restriction fragment length polymorphism analysis. This analysis showed that restriction sites within the gene were highly conserved. The lack of variation for the other restriction sites within the gene indicates that PsaA is genetically conserved, an important characteristic necessary for a candidate common protein vaccine.

A pneumnococcal polysaccharide vaccine was developed with 23 types of pneumococcal bacteria which cause 88 percent of bacteremic pneumococcal disease. Vaccinated, healthy adults are protected from some or all pneumococcal pneumonia bacteria types. However, the carriage rates of the organism do not decline significantly in vaccinated people. Additionally, adverse reactions from this vaccine may occur in older persons, children under the age of two years, and those stricken with long-term illnesses. Furthermore, it is found that the polysaccharide vaccine fails to provide protection in young children, the elderly and the immunocompromised. This led to development of a second-generation protein-conjugate vaccine. This vaccine, composed of the seven most frequent invasive disease-causing capsular serotypes, may overcome the problems of poor immunogenicity associated with the 23-valent vaccine. However, there are indications that this protein-conjugate vaccine may not prevent replacement carriage of serotypes not contained in the vaccine (Mbelle et al. 1997. "Immunogenicity and impact on carriage of 9-valent pneumococcal conjugate vaccine given to infants in Soweto, South Africa", Abstr. L8–12, p. 13, In Abstracts of the 37*th* Interscience Conference on Antimicrobial Agents and Chemotherapy, American Society for Microbiology, Washington, D.C.; Obaro et al. 1996. "Carriage of pneumococci after pneumococcal vaccination", Lancet 348:271–272). These concerns, along with reports of an increase in antibiotic-resistant pneumococci (Centers for Disease Control and Prevention, 1997), have shifted interest toward the development of a vaccine based on immunogenic pneumococcal species-common proteins of S. pneumoniae. The most promising of these proteins include pneumococcal surface adhesin A (Russell et al. 1990, "Monoclonal antibody recognizing a species-specific protein from Streptococcus pneumoniae", J. Clin. Microbiol. 28:2192–2195).

PsaA is under study both as vaccine immunogen and as a reagent for diagnostic assay development (Tharpe et al. 1998, "Comparison of a pneumococcal common protein (PsaA) antibody ELISA and a PsaA immune complex ELISA for detection of pneumococcal serum antibody", Pathobiology, 66:77–83). Monoclonal antibody studies suggest that PsaA is expressed on all 90 serotypes of S. pneumoniae (Crook et al. 1998, "Immunoreactivity of five monoclonal antibodies against the 37-kilodalton common cell wall protein (PsaA) of Streptococcus pneumoniae", Clin. Diagn. Lab. Immunol. 5:205–210) and polymerase chain reaction-restriction fragment length polymorphism (PCR-RFLP) analysis of the 23 vaccine serotypes demonstrated the conservation of the psaA gene (Russell et al. 1990).

A culture assay is currently the Gold Standard for detecting Streptococcus pneumoniae. Patient sputum, throat swab, or blood specimens can be cultured for Streptococcus pneumoniae if they are handled correctly. Such diagnostic tests, however, are generally time-consuming, requiring at least overnight incubation. Furthermore, cultures also lack the certainty of positive identification, providing positive diagnoses only 20% to 30% of the time. Thus the current Gold Standard diagnostic assay has important deficiencies associated with it. Because of the speed with which streptococcal pneumoniae can develop and potentially lead to death, there is a need for rapid testing resulting in earlier treatment of infection. This has the potential to significantly abbreviate the course of the disease and reduce mortality.

Rapid assays for Streptococcus are available in a number of formats. Older format kits involve the use of a multistep latex agglutination procedure or an ElA format, and employ samples such as serum, whole blood, or sputum swabs. Most take less than eight minutes to perform, and show results through the appearance of a colored visual indicator.

In order to detect all 90 serotypes of S. pneumoniae using currently employed procedures, assay reagents representing the 90 different components, such as are used in serologic assays including latex agglutination and counterimmunoelectrophoresis, would be needed. Pneumococcal diagnostic assays are based primarily on detection of pneumococci, pneumococcal antigens, DNA or RNA in blood or body fluids. Although blood culture is currently the most accurate method by which to diagnose pneumococcal disease, only approximately 30% of specimens test positive with this method (Kalin et al. 1983, "Diagnosis of pneumococcal pneumonia: a comparison between microscopic examination of expectorate, antigen detection, and cultural procedures", Scand. J. Infect. Dis. 15:247–255). Conventional serologic methods lack uniform diagnostic sensitivity and specificity and are time-consuming because they require reagents in which all serotypes are represented. Although PCR assays have been reported in the literature (Toikka et al. 1998, "Pneumolysin PCR-based diagnosis of invasive pneumococcal infection in children", J. Clin. Microbiol. 37:633–637), they have not been widely adapted for use in the clinical laboratory because they have not been shown to be consistently and uniformly sensitive. Toikka et al. (1998), for example, described the necessity of testing three different blood fractions to maximize sensitivity. They also suggested that a combination of other diagnostic methods is needed for diagnosis of invasive pneumococcal disease.

Automated serological testing is used in diagnostic testing for Streptococcus pneumoniae infection. These assays identify and quantify the existence of antibodies to bacterial pathogens. All antibody detecting assays may miss active infection if the level of antibodies in a patient's blood is too low, as occurs with certain immunocompromised individuals, or if infection is too recent for antibodies to have been produced. Additionally, as with all antibody-based assays, because levels of antibodies produced against a previous infection fall slowly, testing may indicate an infection that no longer exists.

Thus, there remains a need for an universal, highly sensitive, and highly species-specific method of detection that will permit straightforward and reliable diagnosis of pneumococcal disease. There is further a need for specific reagents that enable universal and specific assays for *Streptococcus pneumoniae* to be carried out. There further remains a need for polypeptides that are immunogenic for stimulating an immune response against *Streptococcus pneumoniae*. Additionally there remains a need for a nucleic acid that includes a sequence encoding such an immunostimulatory polypeptide. The present invention recognizes these needs, and provides compositions and methods based on psaA genes and PsaA polypeptides to address these needs.

SUMMARY OF THE INVENTION

The present invention discloses, in a first aspect, an oligonucleotide including a sequence chosen from among SEQ ID NO:1, SEQ ID NO:2, the complement of SEQ ID NO:1, and the complement of SEQ ID NO:2. In advantageous embodiments, the oligonucleotide may include SEQ ID NO:1, or SEQ ID NO:2.

In a second aspect, the invention discloses a pair of oligonucleotide primers that prime the universal and specific amplification of a nucleic acid that includes at least a portion of the psaA gene of *Streptococcus pneumoniae*. In important embodiments of the oligonucleotide pair, one oligonucleotide of the pair includes the sequence given by SEQ ID NO:1, and the second oligonucleotide of the pair includes the sequence given by SEQ ID NO:2.

In a third aspect, the invention relates to a diagnostic kit for the specific diagnosis of *Streptococcus pneumoniae* that includes reagents for amplification of a nucleic acid, as well as a pair of oligonucleotide primers that prime the universal and specific amplification of a nucleic acid containing at least a portion of the psaA gene of *Streptococcus pneumoniae*. In a significant embodiment of the kit, one oligonucleotide of the pair includes the sequence given by SEQ ID NO:1, and the second oligonucleotide of the pair includes the sequence given by SEQ ID NO:2. In an additional significant embodiment, the kit further includes a second primer pair wherein one oligonucleotide of the pair comprises the sequence given by SEQ ID NO:2, and the second oligonucleotide of the pair comprises the sequence given by SEQ ID NO:3.

In a further aspect of the invention, a method of specifically detecting the presence of *Streptococcus pneumoniae* in a biological sample is disclosed. The method includes the steps of:

(i) obtaining a biological sample from a subject suspected of harboring a serotype of *Streptococcus pneumoniae*;

(ii) contacting at least a portion of the biological sample with a pair of oligonucleotide primers that prime the universal and specific amplification of a nucleic acid including at least a portion of the psaA gene of *Streptococcus pneumoniae* to provide an amplification precursor composition;

(iii) treating the amplification precursor composition under conditions that promote amplification to provide a nucleic acid amplicon containing at least a portion of the psaA gene; and (iv) detecting whether the amplicon is present; whereby, if the amplicon is determined to be present, the sample contains *Streptococcus pneumoniae*. In an advantageous embodiment of the method, an enrichment step is conducted on the biological sample obtained in step (i) prior to the contacting of step (ii). In an additional advantageous embodiment of the method, in step (ii) one oligonucleotide of the pair includes the sequence given by SEQ ID NO:1, and the second oligonucleotide of the pair includes the sequence given by SEQ ID NO:2; additionally a second primer pair may further be included in step (ii), in which one oligonucleotide of the pair includes the sequence given by SEQ ID NO:2, and the second oligonucleotide of the pair includes the sequence given by SEQ ID NO:3

In yet an additional aspect, the present invention discloses an isolated nucleic acid including a nucleic acid amplicon obtained when nucleic acid from a serotype of *Streptococcus pneumoniae* is contacted with a pair of oligonucleotide primers that prime the universal and specific amplification of at least a portion of the psaA gene of *Streptococcus pneumoniae* and the *Streptococcus pneumoniae* nucleic acid so primed is amplified to provide the amplicon which thereby includes the portion of the psaA gene. In an important embodiment, the portion of the psaA gene is operably linked to control elements that promote the expression of a polypeptide comprising the portion of the PsaA protein of a serotype of *Streptococcus pneumoniae* encoded by the gene.

In still a further aspect, the invention discloses a polypeptide including an amino acid sequence encoded by a nucleic acid amplicon that includes at least a portion of the psaA gene obtained when nucleic acid from a serotype of *Streptococcus pneumoniae* is contacted with a pair of oligonucleotide primers that prime the universal and specific amplification of the at least a portion of the psaA gene of *Streptococcus pneumoniae* and the *Streptococcus pneumoniae* so primed is amplified to provide the amplicon.

In yet another aspect, the invention discloses a method of stimulating an immune response against a serotype of *Streptococcus pneumoniae* in a mammal including administering to the mammal an amount of a polypeptide effective to stimulate the immune response, wherein the polypeptide includes an amino acid sequence encoded by a nucleic acid amplicon including at least a portion of the psaA gene obtained when nucleic acid from a serotype of *Streptococcus pneumoniae* is contacted with a pair of oligonucleotide primers that prime the universal and specific amplification of the portion of the psaA gene of *Streptococcus pneumoniae* and the *Streptococcus pneumoniae* so primed is amplified to provide the amplicon.

In still an additional aspect, the invention discloses a method of stimulating an immune response against a serotype of *Streptococcus pneumoniae* in a mammal including administering to the mammal a nucleic acid including a nucleic acid amplicon including at least a portion of the psaA gene obtained when nucleic acid from a serotype of *Streptococcus pneumoniae* is contacted with a pair of oligonucleotide primers that prime the universal and specific amplification of the portion of the psaA gene of a serotype of *Streptococcus pneumoniae* and the *Streptococcus pneumoniae* so primed is amplified to provide the amplicon, wherein the amount of the nucleic acid administered is effective to express an immunostimulatory amount of the portion of the PsaA protein of a serotype of *Streptococcus pneumoniae* encoded by the amplicon in cells of the mammal.

DETAILED DESCRIPTION OF THE INVENTION

As used herein, "universal" designates a process or relates to a composition that is effective for carrying out the objectives of the present invention as they relate to at least a portion of the psaA gene of *Streptococcus pneumoniae* or at least a portion of the PsaA gene product encoded by the gene or portion thereof, regardless of the serotype or strain of *S. pneumoniae*, within the limits of the serotypes or strains disclosed herein. At the time of the present invention, 90 serotypes or strains are known. These are serotypes 1, 2, 3, 4, 5, 6A, 6B, 7F, 7A, 7B, 7C, 8, 9A, 9L, 9N, 9V, 10F, 10A, 10B, 10C, 11F, 11A, 11B, 11C 11D, 12F, 12A, 12B, 13, 14, 15F, 15A, 15B, 15C, 16F, 16A, 17F, 17A, 18F, 18A, 18B, 18C, 19F, 19A, 19B, 19C, 20, 21, 22F, 22A, 23F, 23A, 23B, 24F, 24A, 24B, 25F, 25A, 27, 28F, 28A, 29, 31, 32F, 32A, 33F, 33A, 33B, 33C 33D, 34, 35F, 35A, 35B, 35C, 36, 37, 38, 39, 40, 41F, 41A, 42, 43, 44, 45, 46, 47F, 47A, and 48. Thus, for example, primer set P1 and P2 are universal since they amplify each of the ninety known serotypes of *Streptococcus pneumoniae*.

The terms "specific to" or "specific for" a target sequence, in relation to a nucleic acid sequence such as an oligonucleotide sequence, relate to a nucleotide sequence that hybridizes, under conditions used in given experimental circumstances, to the target but does not hybridize under those circumstances to sequences that are not target sequences. As used herein, "specific" amplification relates to the ability of a primer pair to promote the amplification of a segment of a nucleic acid originating from any of the 90 serotypes of *Streptococcus pneumoniae*, and the inability of the primer pair to promote the amplification of any segment of a nucleic acid originating from another species. Nucleotide sequences that are specific for a particular target, such as the *Streptococcus pneumoniae* nucleotide sequences that are included in the subject matter of the present invention, include sequences every one of whose bases is complementary to the corresponding base on the target.

Furthermore, as used herein, "specificity" of a nucleic acid sequence for a target sequence also encompasses nucleic acids and oligonucleotides in which a small number of nucleotides may not be complementary to the corresponding nucleotide of the target sequence. Such sequences are still "specific" for the target sequence, as used herein, as long as the extent of deviation from complementarity remains functionally of little consequence, since they still hybridize to the target. In particular, such a sequence is "specific" for the target sequence as long as it hybridizes effectively to the target sequence but does not hybridize to non-target sequences, under the conditions used in given experimental circumstances. Deviation from complete complementarity may underlie a weaker extent of hybridization of a primer to the target sequence under given experimental conditions. Under such circumstances, the yield of the amplicon produced when such a primer is used may be poor. Nevertheless a finding that an amplicon has been produced, regardless of its amount, is sufficient for the purposes of the present invention to conclude that the target sequence is present.

Specific amplification methods for nucleic acids are widely available in the fields of molecular biology and clinical microbiology. For example, the polymerase chain reaction (PCR) can be used to amplify nucleic acid in a sample. Other amplification techniques can be used to detect the presence of *Streptococcus pneumoniae* in a sample, such as ligase chain reaction (LCR), the self-sustained sequence replication (3SR) system, the transcription-based amplification system (TAS), and the RNA replication system based on Qβ replicase.

Preferably, the amplification procedure used in the present invention is PCR. As used herein the terms "polymerase chain reaction" or "PCR" relate to a procedure whereby a limited segment of a nucleic acid molecule, which frequently is a desired or targeted segment, is amplified repetitively to produce a large amount of DNA molecules which consist only of the segment. PCR and the other amplification procedures are described in operational detail in, for example, "Molecular Cloning: A Laboratory Manual", 2nd Ed., Sambrook, Fritsch and Maniatis, Cold Spring Harbor Laboratory, Cold Spring Harbor, N.Y., 1989; "Current Protocols in Molecular Biology", Ausubel et al., John Wiley and Sons, New York 1987 (updated quarterly); and in U.S. Pat. No. 4,965,188. Additional guidance concerning PCR and related methods can be found in, for example, U.S. Pat. Nos. 4,683,202; 5,578,467; 5,545,522; and 5,624,833. The references cited in this paragraph are specifically incorporated by reference As used herein the term "primer" or "oligonucleotide primer" relates to an oligonucleotide that includes a specific or desired nucleotide sequence which is complementary to a particular sequence on one of the strands of a DNA duplex. When the primer is caused to hybridize to the specific sequence in a DNA duplex to which it is complementary, it may serve as the priming position, or the initiation position, for the action of a primer-dependent DNA polymerase activity. The primer, once hybridized, acts to define one end of the operation of the transcription activity of the polymerase on the duplex. A specific pair of primers is employed, wherein each hybridizes to one of the strands such that transcription, which proceeds from the 5'- end to the 3'- end, is in the direction leading to the site of hybridization of the second primer on the opposite strand of the duplex. After several rounds of hybridization and transcription the amplified DNA produced is a segment having a defined length whose ends are defined by the sites to which the primers hybridize.

As used herein, a "vector" relates to a nucleic acid which functions to incorporate a particular nucleic acid segment, such as a sequence including a particular gene, into a cell. In most cases, the cell does not naturally contain the gene, so that the particular gene being incorporated is a heterologous gene. A vector may include additional functional elements that direct and regulate transcription of the inserted gene or fragment. The regulatory or control sequence is operably positioned with respect to the protein-encoding sequence such that, when the vector is introduced into a suitable host cell and the regulatory sequence is triggered, the protein encoded by the gene is expressed. Regulatory or control sequences may include, by way of non-limiting example, a promoter, regions upstream or downstream of the promoter such as enhancers that may regulate the transcriptional activity of the promoter, and an origin of replication. A vector may additionally include appropriate restriction sites, antibiotic resistance, or other markers for selection of vector containing cells, RNA splice junctions, a transcription termination region, and so forth.

The invention provides oligonucleotide primers which, when used in specified pairs in a nucleic acid amplification protocol applied to a nucleic acid originating from any of the 90 serotypes or strains of Streptococcus pneumoniae, promote the preparation of an amplicon having approximately the same size, in terms of number of bases contained therein, regardless of the serotype or strain subjected to the amplification protocol. The primers were designed based on the nucleotide sequence of a nucleic acid comprising the psaA gene from strain 6B of Streptococcus pneumoniae, as disclosed in U.S. Pat. No. 5,854,416 (incorporated herein by reference in its entirety). One of the primers employed in the present invention (i.e., P3, having the sequence AGGATCTAATGAAAAAATTAG (SEQ ID NO:3; priming forward sense replication)) is also disclosed in U.S. Pat. No. 5,854,416. The remaining two primers (i.e., the universal primers) include the sequences CTTTCTGCAATCAT-TCTTG (SEQ ID NO:1; primer P1, priming forward sense replication) and GCCTTCTTTACCTTGTTCTGC (SEQ ID NO:2; primer P2, priming reverse sense replication). The primer pair P1 and P2 is universal and specific for the amplification of a segment of the nucleic acid from all 90 serotypes or strains of Streptococcus pneumoniae that includes at least a portion of the psaA gene.

The present invention relates in an important aspect to carrying out a diagnostic assay for the presence of Streptococcus pneumoniae in a biological samples. Among the sources for such samples, it is envisioned to acquire samples of nasopharyngeal secretions, ear fluid, blood, a blood fraction, sputum, or tracheal aspirates, by way of nonlimiting example.

The diagnostic assay employs specific primer pairs formulated from the oligonucleotide primers disclosed herein to amplify at least a portion of the psaA gene of any serotype of Streptococcus pneumoniae that may be present in a biological sample. In one preferred embodiment, the primer pair is composed of oligonucleotides that include the sequences of SEQ ID NO:1 (forward amplification) and SEQ ID NO:2 (reverse amplification). Amplicons provided by the use of this primer pair contain approximately 838 bases, and provide a universal and specific assay for Streptococcus pneumoniae. In a second preferred embodiment, primer pairs composed of oligonucleotides that include the sequences of SEQ ID NO:1 (forward amplification) and SEQ ID NO:2 (reverse amplification) as well as including the sequences of SEQ ID NO:3 (forward amplification) and SEQ ID NO:2 (reverse amplification), providing amplicons having approximately 838 and 867 bases, respectively, may be used. In the assays, the presence of amplicons after carrying out an amplification procedure permits the operator to conclude that the biological sample contains a serotype of Streptococcus pneumoniae.

The methods available for detecting the presence of the amplicon include the following procedures, by way of nonlimiting example. To begin with, the size of the amplicon may be determined by a procedure such as gel electrophoresis or comparable size-determining method to ensure its size is commensurate with the anticipated product. The presence of the amplicon may be determined using conventional techniques and procedures. For example, the primers can be radioactively labeled such that the amplification product containing these labeled primers are detectable by the radioactive decay of the label. Alternatively, the primers can be labeled to contain other detectable moieties, such as biotin. When biotin is used, it is further labeled and detected by means of a labeled form of avidin or streptavidin. Still further, gel electrophoresis procedures can be used and the amplified nucleic acid can be stained and visualized (e.g., ethidium bromide staining). Alternatively, labeled probes, designed to hybridize with sequences unique to the amplified product, can be used to detect the presence of the amplified product.

The diagnostic assays disclosed herein provide the advantage, heretofore unknown in the field of diagnosing Streptococcus pneumoniae infection, of specifically detecting all of the 90 serotypes of Streptococcus pneumoniae currently known using a single assay with a single set of reagents. These reagent sets can include primers P1 and P2, or primers P1, P2, and P3 employed as the primer pairs specified herein. This detection proceeds with high sensitivity and great economy. These assays therefore represent a significant advance over the currently available diagnostic assays for Streptococcus pneumoniae which rely on capsular polysaccharide antigen combinations, and which frequently provide false negative determinations.

In an additional aspect, the present invention relates to nucleic acids containing the amplicon obtained when a nucleic acid from a serotype of Streptococcus pneumoniae is contacted with a pair of oligonucleotide primers that prime the universal amplification of at least a portion of the psaA gene of a serotype of Streptococcus pneumoniae and the Streptococcus pneumoniae so primed is amplified to provide the amplicon. As disclosed herein, such amplicons may be produced using the primer pair (i.e., P1 and P2) composed of oligonucleotides that include the sequences of SEQ ID NO:1 (forward amplification) and SEQ ID NO:2 (reverse amplification) providing amplicons containing approximately 838 bases. Additionally, another assay can be carried out using the primer pair (i.e., P3 and P2) composed of oligonucleotides that include the sequences of SEQ ID NO:3 (forward amplification) and SEQ ID NO:2 (reverse amplification), providing amplicons predicted to have approximately 867 bases. Such amplicons have beneficial applications in systems that may be used to express the polypeptides encoded by them. These polypeptides, containing at least a portion of the PsaA surface protein, are useful as antigens and immunogens related to infection by Streptococcus pneumoniae. They additionally are useful when incorporated into nucleic acid vectors that may be used directly in a host as an immunogen-producing nucleic acid.

The preferred methods and assays employ the universal primer pair (i.e., P1 and P2) alone. However, and as discussed in more detail below (see Examples 1 and 2), at least one specific sample of a serotype (i.e., a sample of serotype 16F obtained from ATCC) failed to produce the expected amplicon with the P1/P2 primer pair. A characteristic amplicon could, however, be obtained from this sample using the second primer pair P3/P2. Thus, when used, the second prier pair, which is designed to be used in conjunction with the universal primer pair, could also be used.

In order to express the psaA gene or portion thereof contained in the nucleic acid amplicon, the amplicon is introduced into a vector, such as a plasmid or virion, in such a way that it is operably linked to control elements in the nucleic acid of the vector. The control elements promote the expression of the polypeptide when the nucleic acid is introduced into a suitable host cell and the cell is cultivated under conditions that promote expression of the protein. The polypeptide synthesized includes at least a portion of the PsaA protein of a serotype of Streptococcus pneumoniae encoded by the gene. Procedures to be used in preparing such vectors, in transducing bacteria or transfecting eukaryotic cells with such vectors, and expressing the PsaA or portion thereof using the recombinant cells so produced, are known to workers of skill in molecular biology and clinical microbiology, and are disclosed, for example, in Sambrook et al. and Ausubel et al.

The invention additionally relates to the PsaA polypeptide comprising an amino acid sequence encoded by the nucleic acid amplicons obtained when nucleic acids from various serotypes of Streptococcus pneumoniae are contacted with a pair of oligonucleotide primers that prime the universal amplification of at least a portion of the psaA gene of a serotype of Streptococcus pneumoniae and the Streptococcus pneumoniae so primed is amplified to provide the amplicon. This polypeptide is useful, for example, as a probe in enzyme immunoassay intended to detect the presence of anti-Streptococcus pneumoniae antibodies in a biological sample, as well as an antigen or immunogen to stimulate an immune response or a protective immune response, respectively, in a mammal to which the polypeptide is administered. In particular, the invention relates to a method of stimulating an immune response against serotypes of Streptococcus pneumoniae in a host comprising administering to the host an immunogenically effective amount of a polypeptide comprising an amino acid sequence encoded by a nucleic acid amplicon obtained when a serotype of Streptococcus pneumoniae is contacted with a pair of oligonucleotide primers that prime the universal amplification of at least a portion of the psaA gene of a serotype of Streptococcus pneumoniae and the Streptococcus pneumoniae so primed is amplified to provide the amplicon.

This invention additionally relates to using the amplicons obtained as described above, when incorporated into suitable vectors, as nucleic acid vaccines that elicit protection against Streptococcus pneumoniae infection in a mammal. In particular, the invention discloses a method of stimulating an immune response against serotypes of Streptococcus pneumoniae in a mammal in which an amount of a nucleic acid comprising a nucleic acid amplicon obtained when a nucleic acid from a serotype of Streptococcus pneumoniae is contacted with a pair of oligonucleotide primers that prime the universal amplification of at least a portion of the psaA gene of a serotype of Streptococcus pneumoniae and the Streptococcus pneumoniae so primed is amplified to provide the amplicon, is administered to the host. The vector including the amplicon is appropriately structured such that when incorporated into the cells of a host organism, such as a human or other mammal intended to be vaccinated, the vector interacts with the naturally occurring components of the cell such that the vector promotes the expression of the PsaA polypeptide or portion thereof encoded by the amplicon. The amount of the nucleic acid administered is effective to express an immunogenic amount of at least a portion of the PsaA protein encoded by the amplicon in the cells of the mammal.

The following examples are intended to illustrate the development and implementation of the invention and not to limit it.

EXAMPLE 1

Amplification of Serotypes of Streptococcus pneumoniae Using Primers of SEQ ID NOs:1 and 2

The 90 S. pneumoniae serotypes as outlined by Henrichsen (1995, "Six newly recognized types of Streptococcus pneumoniae", J. Clin. Microbiol. 33:2759–2762) were obtained from the Statens Seruminstitut, Copenhagen, Denmark; the American Type Culture Collection (ATCC); and the Streptococcal Reference Laboratory, Centers for Disease Control and Prevention (CDC), Atlanta, Ga.

PCR.

Bacterial strains were grown for isolation on Trypticase soy agar plates supplemented with 5% defibrinated sheep blood for 12 h at 37° C. in $CO_2$. For PCR amplification, approximately 5 CFUs were placed directly into a PCR reaction mixture and allowed to lyse in the thermocycler. If this method failed to produce an amplified product, whole cells were boiled in 200 μL of filtered water for 10 minutes, followed by a cooling time on ice for at least 5 minutes. An aliquot of boiled lysate was then used in the PCR reaction mixture.

Primers.

The sequences of the primers used to amplify psaA were as follows: 5'CTTTCTGCAATCATTCTTG3' (P1; SEQ ID NO:1) as the forward primer and 5'GCCTTCTTTACCT-TGTTCTGC3' (P2; SEQ ID NO:2) as the reverse primer. These primers, as well as primer P3 (SEQ ID NO:3 ), were designed from the nucleic acid sequence data obtained from serotype 6B (GenBank # U53509; Sampson et al. 1997). All primers were prepared at the Biotechnology Core Facility at CDC.

The PCR reaction mixture (100 μL) contained 100 ng of each primer (P1 and P2), 2.0 μL of 10 mM dNTPS (Boehringer Mannheim, Indianapolis, Ind.), 10.0 μL 10 mM $MgCl_2$, 50.0 μL of PCR Master Mix (Boehringer Mannheim), approximately 5 CFUs of bacteria, or 10 μL of boiled lysate. Amplification was performed in a Thermal Cycler 480 (Perkin-Elmer, Norwalk, Conn.) for 35 cycles, (95° C., 0.5 min; 52° C., 0.5 min; 72° C., 2.0 min for denaturing, annealing, and extension, respectively), with final extension at 72° C. for 8.0 min. Negative controls contained the PCR mixture without the template DNA. The positive control contained serotype 6B DNA as template DNA.

Approximately 10 μL of each PCR amplicon was electrophoresed on a 1.0% agarose gel and subsequently stained with ethidium bromide and visualized with a UV transilluminator. Primers P1 and P2 as designed are expected to yield a 838-bp fragment. Amplified product size was determined by comparison with a 1-kb DNA ladder molecular marker (Life Technologies, Rockville, Md.).

Figure 1:
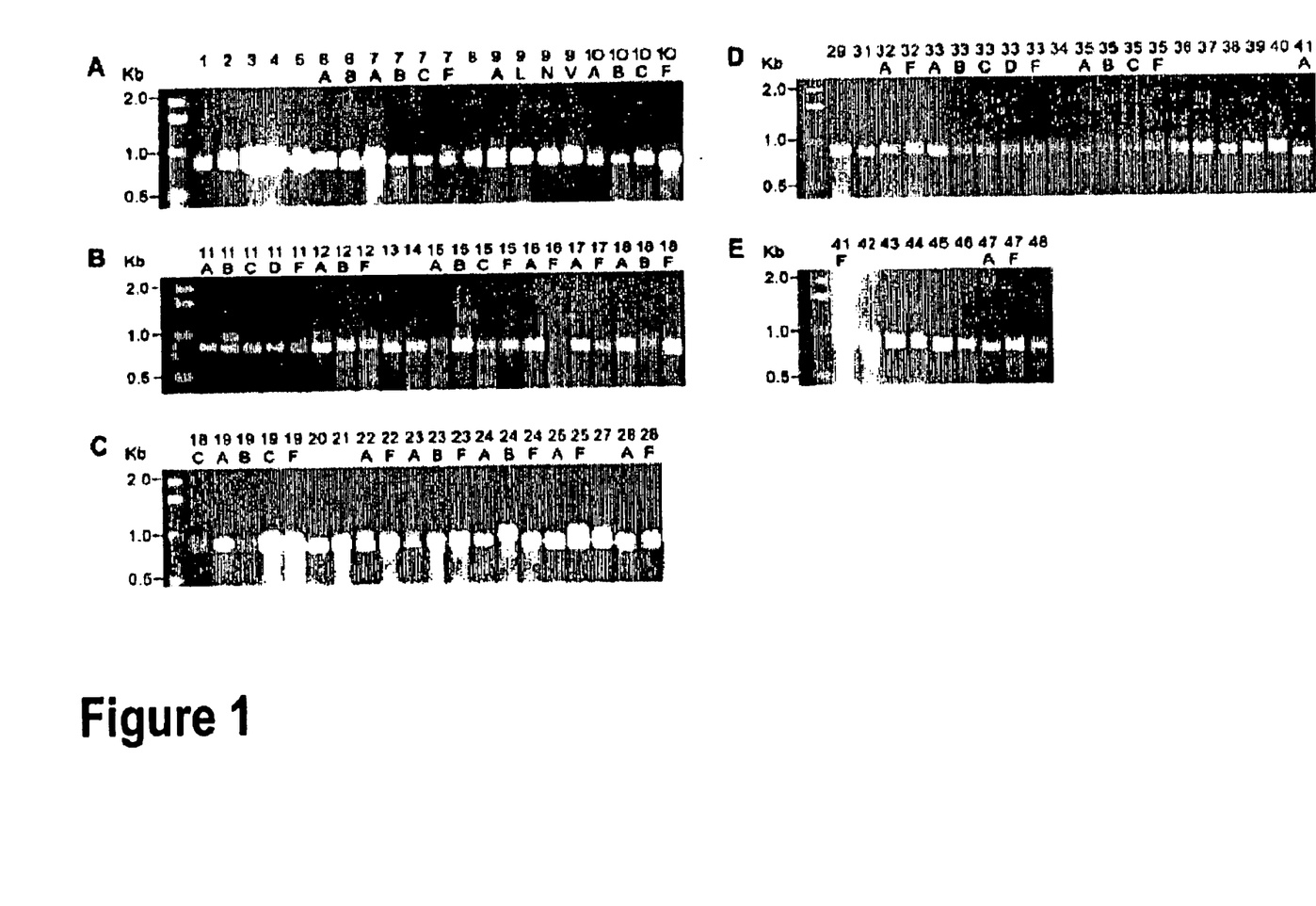
FIGS. 1A-1E. Amplification of 90 *S. pneumoniae* serotypes using primers P1 and P2, providing an 838 bp fragment analyzed by agarose gel electrophoresis of the PCR-amplified products. Serotype designations are indicated above the lanes. Panel A, serotypes 1–10F; Panel B, serotypes 11A–18F; Panel C, 18C–28F; Panel D, serotypes 29–41A; and Panel E, serotypes 41F–48.

The initial assays using primers P1 and P2 showed that psaA was amplified in 89 of the 90 S. pneumoniae serotypes (FIG. 1). Amplification resulted in a 838 bp fragment as expected. However, one sample, ATCC serotype 16F (ATCC# 6316,) was not amplified with this primer pair. As shown in Example 2, this result appears to be unique for this particular isolate; other isolates of 16F were successfully amplified by P1 and P2. Thus, amplification using primer pair P1 and P2 successfully amplifies all 90 serotypes currently known and presently tested.

EXAMPLE 2

Amplification of Isolates of Serotype 16F of Streptococcus pneumoniae

Figure 2:
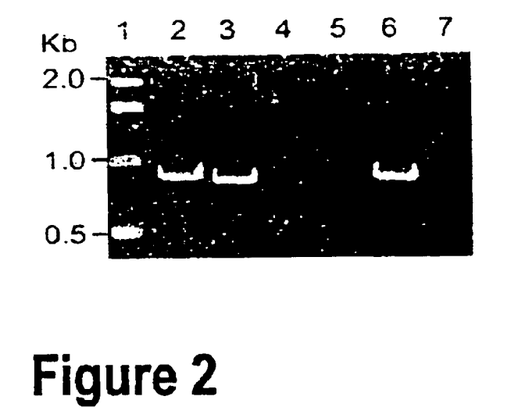
FIG. 2. Amplification of ATCC 16F using different primer pairs. Lane 1, DNA marker; Lane 2, serotype 6B amplified with P3 and P2; Lane 3, serotype 6B amplified with P1 and P2; Lane 4, negative control amplified with P3 and P2; Lane 5, negative control amplified with P1 and P2; Lane 6, serotype 16F (ATCC# 6316) amplified with P3 and P2; Lane 7, serotype 16F (ATCC# 6316) amplified with P1 and P2.

Using the assay procedure described in Example 1, amplification of the isolate of serotype 16F (ATCC# 6316) using primer pair P1 and P2 was not successful. Using the forward primer, P3, 5'AGGATCTAATGAAAAAATTAG3', with primer P2, successful amplification was observed. P3 is derived from a highly conserved region at the 5' end of the psaA gene (Russell et al. 1990). It is predicted that primers P3 and P2 yield a 867-bp amplicon. FIG. 2 shows that serotype 16F (ATCC# 6316) provides an amplicon when primed with the pair P3/P2 (Lane 6).

Figure 3:
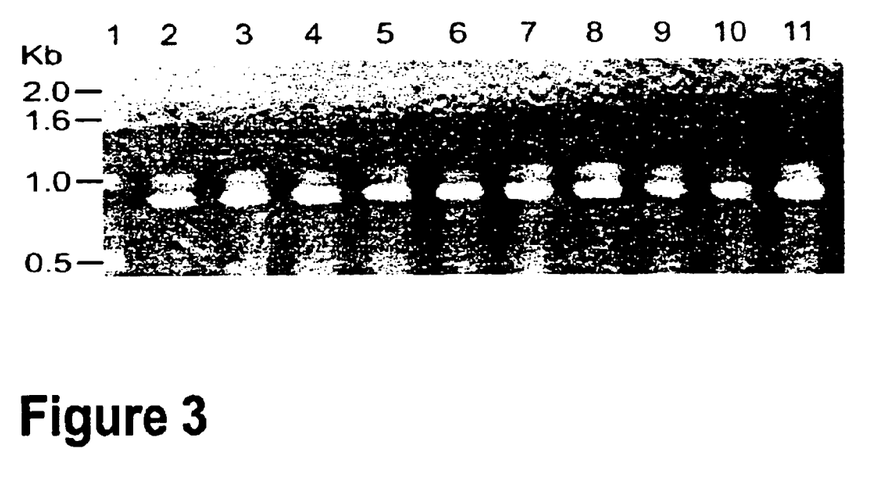
FIG. 3. Amplification of 16F clinical isolates using oligonucleotide primers P1 and P2. Agarose gel electrophoresis of PCR amplified products from *S. pneumoniae* serotype 16F clinical isolates, Lane 1. DNA markers; Lanes 2–11, amplified clinical strains.

To determine if the inability of P1 and P2 primers to amplify this isolate of 16F was common to all strains of serotype 16F, 10 clinical strains of serotype 16F from the United States (provided by The Streptococcal Reference Laboratory (CDC, Atlanta, Ga.)) and 10 clinical 16F isolates from Brazil (provided by Drs. Maria Christina de C Brandileone and Claudio Sacchi, Instituto Adolfo Lutz, Brazil) were tested with the primers. All 20 clinical strains were amplified using the primers P1 and P2 (see FIG. 3, which shows the results for the 10 samples obtained in the United States). This indicates that the lack of amplification of the one ATCC isolate of 16F, when primed with P1/P2, identified in Example 1 was peculiar to that strain of 16F and not to all 16F serotypes.

To ascertain if there were significant differences within the sequence of the ATCC serotype 16F isolates compared with that of serotype 6B, the DNA sequence of ATCC 16F psaA (De, B., unpublished data) was compared with primer sequences P1 and P2. There was a six-base region of variability between the ATCC 16F sequence and 6B sequence within the 19-base P1 primer binding site. Therefore, ATCC serotype 16F may be a genetic variant which may have acquired mutations within the gene through recombination with other species.

EXAMPLE 3
Amplification of Isolates of Serotype 16F of *Streptococcus pneumoniae*

The specificity of the primers used in the PCR assay was tested using various bacteria, including heterologous upper respiratory bacteria. The Streptococcal Reference Laboratory (CDC, Atlanta, Ga.) provided clinical isolates of the heterologous species, *Streptococcus mitis*, *S. oralis*, *S. parasanguinis*, *S. sanguinis*, *S. crista*, *S. gordonii*, *S. vestibularis*, *S. salivarius*, various β-hemolytic strains of *Streptococcus pyogenes*. In addition, heterologous genera, *Staphylococcus aureus*, *Enterococcus faecalis*, *Corynebacterium minutissimum*, *Corynebacterium pseudodiphtheriticum*, *Corynebacterium xerosis*, *Corynebacterium pseudotuberculosis*, *Staphylococcus epidermidis*, *Klebsiella pneumoniae*, *Escherichia coli*, *Moraxella catarrhalis*, and *Haemophilus influenzae* were also obtained from the Streptococcal Reference Laboratory. Eleven multidrug-resistant strains of *S. pneumoniae* were provided by the Pneumococcal Molecular Epidemiology Network. *Mycobacterium fortuitum*, *Norcardia farcinica*, and *Rhodococcus equi* were provided by the Actinomycetes Reference Laboratory, Meningitis and Special Pathogens Branch, CDC; *Chlamydia pneumoniae*, *Pseudomonas aeruginosa*, and *Mycoplasma pneumoniae* were provided by the Respiratory Diseases Laboratory, Respiratory Diseases Branch, CDC.

These bacteria, including several strains for some of the species, were cultured and subjected to PCR using the universal primer pair P1 and P2. All bacteria tested failed to amplify with the psaA primers (Table 1).

TABLE 1

Heterologous Bacteria Tested (all were PCR negative).

| Organism | No. of strains tested |
|---|---|
| Streptococcal species | |
| *S. mitis* | 7 |
| *S. oralis* | 5 |
| *S. parasanguinis* | 3 |
| *S. sanguinis* | 3 |
| *S. crista* | 4 |
| *S. gordonii* | 5 |
| *S. vestibularis* | 2 |
| *S. salivarius* | 2 |
| Beta-hemolytic Streptococci | |
| *Streptococcus pyogenes* | 1 |
| Group C | 3 |
| Group F | 1 |
| Group G | 5 |
| Non-Streptococcal organisms | |
| *Pseudomonas aeruginosa* | 1 |
| *Chlamydia pneumoniae* | 1 |
| *Mycoplasma pneumoniae* | 1 |
| *Mycobacterium fortuitum* | 1 |
| *Nocardia farcinica* | 1 |
| *Rhodococcus equi* | 1 |
| *Staphylococcus aureus* | 8 |
| *Staphylococcus epidermidis* | 1 |
| *Enterococcus faecalis* | 2 |
| *Corynebacterium minutissimum* | 1 |
| *Corynebacterium pseudodiphtheriticum* | 1 |
| *Corynebacterium xerosis* | 1 |
| *Corynebacterium pseudotuberculosis* | 1 |
| *Klebsiella pneumoniae* | 1 |
| *Escherichia coli* | 2 |
| *Moraxella catarrhalis* | 1 |
| *Haemophilus influenzae* | 1 |

Broad-range PCR primers were designed from bacterial 16S rDNA sequences. These primers were used to confirm that there was bacterial DNA present in the samples.

It is concluded that primer pair P1/P2 is specific for the universal amplification of the *Streptococcus pneumoniae* psaA gene. It is further concluded that false positive results derived from other common bacterial pathogens in a PCR diagnostic assay using these primers will be very unlikely.

EXAMPLE 4
Sensitivity of the Amplification Procedure

The sensitivity of the PCR was evaluated by using pneumococcal DNA as a target in 5-fold dilutions. The sensitivity was about 140 fg as determined by visualization of the 838-bp band in agarose gels (not shown).

EXAMPLE 5
Detection of *Streptococcus pneumoniae* in Clinical Samples

Nasopharyngeal secretions were collected in a blinded manner from children under 5 years of age attending a clinic or emergency room in the United States, China, or Israel. These specimens had no identifiers and were unlinked. The secretions were inoculated into STGG transport medium for transfer to the Centers for Disease Control and Prevention.

For the present assessment, the samples were first enriched as follows. A 10-μL aliquot of the specimen was introduced into 2.0 mL of Todd-Hewitt broth and the suspension was incubated in a tightly capped test tube for 3.5 hours in a 37° C. water bath. The suspension was then centrifuged at 14,000×g for ten minutes in a microcentrifuge (Eppendorf model 5415C). The pellet was washed by resuspending it in 100 μL of ultra-filtered water, and the washed suspension was centrifuged again. The final pellet was resuspended in 50 μL of filtered water and boiled for 10 minutes. After boiling, the suspension was cooled on ice for at least 5 minutes, then used in the psaA-PCR reaction mixture as described in Example 1. In addition, the samples were cultured in conventional fashion to provide diagnostic standard results.

The enrichment step described above was incorporated into the procedure prior to conducting the PCR assay in order to improve sensitivity, since the specimen size was small (20 μL). By so doing, it was found that positive results could be obtained without purification of DNA template. Three of four specimens were determined to be positive for S. pneumoniae by culture. Of these three specimens, two were amplified using the psaA-PCR of the invention. These specimens contained more than ≧25 colonies per 0.1 mL. The third specimen, determined by culture to have fewer than 25 organisms per 0.1 mL, was not detected by psaA-PCR. The fourth specimen was negative by both culture and psaA-PCR. These results demonstrate the usefulness of the present assay in epidemiologic studies to determine carriage of S. pneumoniae or confirm its presence. The use of this simple enrichment step is ideal for maximizing the template concentration when the sample size is limited and allows for testing without performing stringent DNA purification procedures.

On the other hand, many pneumococcal disease patients have received antibiotics for treatment and any available specimens would contain only nonviable organisms. In this case, sample preparation procedures via DNA extraction would be preferable since it would make available DNA from both viable and non-viable organisms.

We claim:

1. An oligonucleotide consisting of a sequence chosen from the group consisting of SEQ ID NO:1, SEQ ID NO:2, the full-length complement of SEQ ID NO:1, and the full-length complement of SEQ ID NO:2.

2. The oligonucleotide described in claim 1 consisting of the sequence set forth in SEQ ID NO:1.

3. The oligonucleotide described in claim 1 consisting of the sequence set forth in SEQ ID NO:2.

4. A pair of oligonucleotide primers, wherein one oligonucleotide of the pair consists of the sequence set forth in SEQ ID NO:1 or the full-length complement thereof, and the second oligonucleotide of the pair consists of the sequence set forth in SEQ ID NO:2 or the full-length complement thereof.

5. A diagnostic kit for the specific diagnosis of *Streptococcus pneumoniae* comprising reagents for amplification of a nucleic acid and a pair of oligonucleotide primers, wherein one oligonucleotide of the pair consists of the sequence set forth in SEQ ID NO:1 or the full-length complement thereof, and the second oligonucleotide of the pair consists of the sequence set forth in SEQ ID NO:2 or the full-length complement thereof.

6. The kit described in claim 5 further comprising a second primer pair wherein one oligonucleotide of the pair consists of the sequence set forth in SEQ ID NO:2, and the second oligonucleotide of the pair consists of the sequence set forth in SEQ ID NO:3.

7. A method of specifically detecting the presence of *Streptococcus pneumoniae* in a biological sample comprising the steps of:

(i) obtaining a biological sample from a subject suspected of harboring a serotype of *Streptococcus pneumoniae*;

(ii) contacting at least a portion of the biological sample with a pair of oligonucleotide primers, wherein one oligonucleotide of the pair consists of the sequence set forth in SEQ ID NO:1 or the full-length complement thereof, and the second oligonucleotide of the pair consists of the sequence set forth in SEQ ID NO:2 or the full-length complement thereof under conditions that promote amplification to provide a nucleic acid amplicon comprising at least a portion of the psaA gene; and (iii) detecting whether the amplicon is present; whereby if the amplicon is present the sample contains *Streptococcus pneumoniae*.

8. The method described in claim 7 wherein an enrichment step is conducted on the biological sample obtained in step (i) prior to the contacting of step (ii).

9. The method described in claim 7 further comprising a second primer pair for use in step (ii), wherein one oligonucleotide of the pair consists of the sequence set forth in SEQ ID NO:2 or the full-length complement thereof, and the second oligonucleotide of the pair consists of the sequence set forth in SEQ ID NO:3 or the full-length complement thereof.

* * * * *

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
ctttctgcaa tcattcttg                                                  19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
gccttcttta ccttgttctg c                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
aggatctaat gaaaaaatta g                                               21